United States Patent [19]
Antikainen et al.

[11] Patent Number: 5,740,601
[45] Date of Patent: Apr. 21, 1998

[54] METHOD OF MANUFACTURING AN IMPEDANCE DETECTOR

[75] Inventors: Veijo Antikainen, Vantaa; Osmo Reittu, Espoo; Ingmar Stuns, Helsinki; Simo Tammela, Espoo; Heikki Turtiainen, Vantaa, all of Finland

[73] Assignee: Vaisala Oy, Vantaa, Finland

[21] Appl. No.: 569,867

[22] Filed: Dec. 8, 1995

[30] Foreign Application Priority Data

Dec. 28, 1994 [FI] Finland ............... 946117

[51] Int. Cl.$^6$ ............... H01C 17/00; H01R 43/00
[52] U.S. Cl. ............... 29/610.1; 29/825
[58] Field of Search ............... 29/825, 610.1; 361/281, 282, 286, 278; 140/92.2, 71.5; 73/29.01, 335.03, 335.02, 29.05

[56] References Cited

U.S. PATENT DOCUMENTS

| | | |
|---|---|---|
| 2,733,324 | 1/1956 | Sabouni ............... 29/613 |
| 3,168,829 | 2/1965 | Nelson . |
| 3,350,941 | 11/1967 | Misevich . |
| 5,359,491 | 10/1994 | Coville et al. ............... 361/282 |
| 5,483,414 | 1/1996 | Turtiainen ............... 361/282 |
| 5,553,495 | 9/1996 | Paukkunen et al. ............... 29/825 |
| 5,557,042 | 9/1996 | Paukkunen et al. ............... 29/825 |

FOREIGN PATENT DOCUMENTS

| | | |
|---|---|---|
| 43775 | 1/1982 | European Pat. Off. . |
| 564428 | 10/1993 | European Pat. Off. . |
| 645606 | 3/1995 | European Pat. Off. . |
| 92439 | 7/1944 | Finland . |
| 48229 | 4/1974 | Finland . |
| 92439 | 7/1994 | Finland . |
| 92440 | 7/1994 | Finland . |
| 92441 | 7/1994 | Finland . |
| 733702 | 2/1995 | Finland . |
| 2052456 | 5/1972 | Germany . |
| 3201643 | 7/1983 | Germany . |

*Primary Examiner*—P. W. Echols
*Attorney, Agent, or Firm*—Jones & Askew

[57] ABSTRACT

The invention concerns an electrical impedance detector for measurement of physical quantities, in particular of temperature or humidity, as well as a process for manufacture of the detectors. The impedance detector is composed of pieces cut off from a continuous detector filament (20). The detector filament (20) comprises an electrically conductive pair of electrode wires (10a,10b) or an equivalent assembly of electrode wires, on/between which there is an active material (11) whose impedance properties are a function of the physical quantity to be measured. The different electrode wires (10a,10b) of the detector filament (20) in the pieces of detector filament (20) have been cut off at different points (41a,41b), compared with one another, so that the impedance (CM) to be measured will be formed in the area (CV) between the cut-off points (41a,41b) of the electrode wires (10a,10b). As the starting material of the active material layer (11') in the detector, a glass paste (11P) is used, through which the pair of electrode wires (10a,10b) is drawn through the drying oven (34) onto the receiving frame (35). The stage of crystallization of the active material layer takes place in a separate heat-treatment stage which takes place after the winding stage.

14 Claims, 5 Drawing Sheets

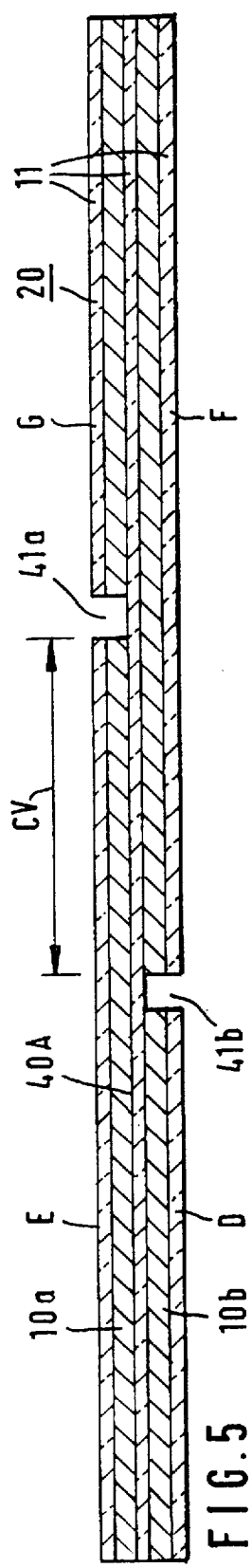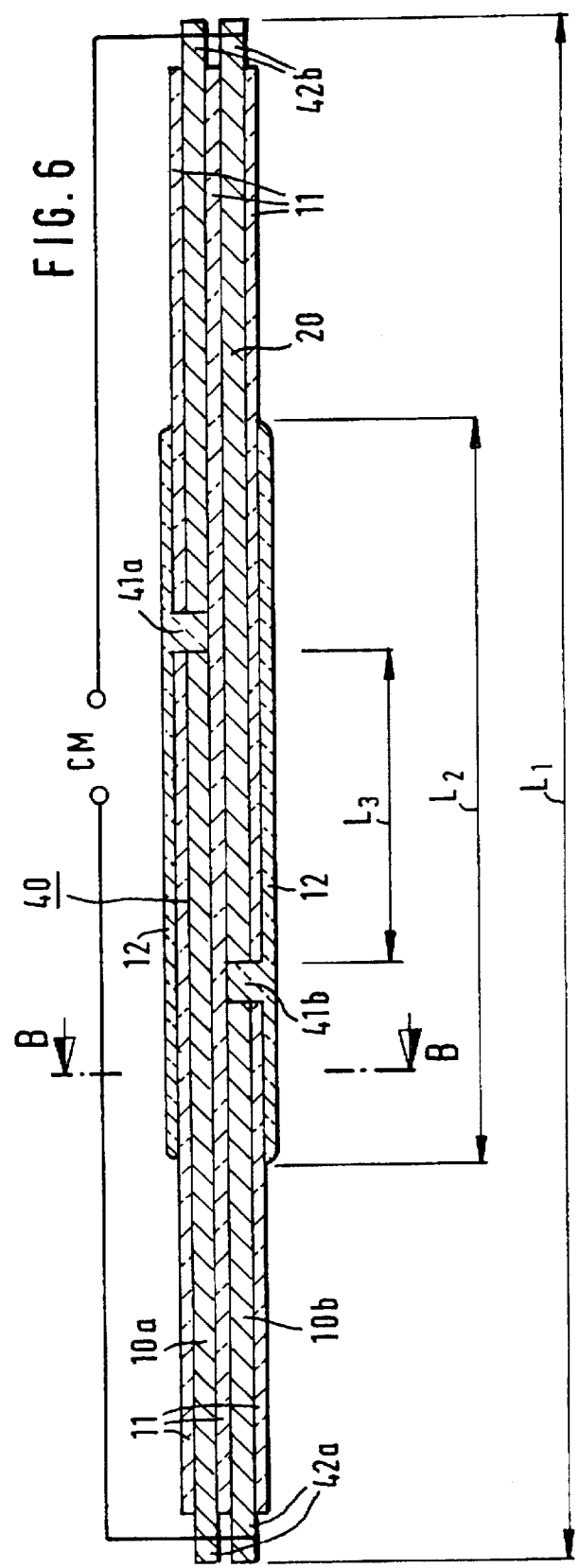

METHOD OF MANUFACTURING AN IMPEDANCE DETECTOR

The invention concerns an electrical impedance detector for measurement of physical quantities, in particular of temperature or humidity, which impedance detector is composed of pieces cut off from a continuous detector filament, and which detector filament comprises an electrically conductive pair of electrode wires or an equivalent assembly of electrode wires, on/between which there is an active material whose impedance properties are a function of the physical quantity to be measured.

Further, the invention concerns a process for manufacture of electrical impedance detectors, said detector being intended for measurement of physical quantities, in particular of temperature or relative humidity, in which process a detector-filament blank is manufactured as a continuous drawing process by using an electrically conductive pair of electrode wires or an equivalent assembly of electrode wires as a carrier wire and as drawing means; and in the process, in a continuous filament process, said pair of electrode wires or assembly of electrode wires is coated with an active material whose impedance properties are a function of the physical quantity to be measured, and, out of the detector filament obtained in the steps defined above, pieces of a length suitable for the purpose of use are cut off, the electrode wires being uncovered from both ends of said filament pieces so as to form electrical contact points for the detector.

In a number of applications, high speed, small size, and low radiation error are required from measurement detectors, in particular from detectors intended for measurement of temperature or relative humidity. Said requirements are particularly strict, e.g., in detectors of radiosondes.

As is known in the prior art, for example, as temperature detectors of radiosondes, as a rule, capacitive detectors are used, whose active material is a ceramic whose dielectricity is dependent on the temperature. The prior-art ceramic and glass-ceramic temperature detectors are, however, of relatively large size, and therefore their speed and radiation error, and also the processes of manufacture, would require some improvement. The radiation error produced by solar radiation has been the most important problem in the temperature measurement by radiosondes with the use of prior-art temperature detectors.

Besides capacitive detectors, in radiosondes and equivalent, resistive detectors and thermoelements have also been used as temperature detectors.

In the prior art, capacitive humidity detectors are known in whose capacitance the dielectric material used is a polymer, a ceramic, or a glass-ceramic whose dielectric constant is a function of the humidity absorbed by it. The speed and corresponding properties of these detectors, and so also the processes of manufacture, also require development, in particular in view of radiosonde applications.

As regards the prior-art electrically detected temperature and humidity detectors, reference is made, e.g., to the U.S. Pat. Nos. 3,168,829 and 3,350,941 as well as to the applicant's FI Patent No. 48,229, in which latter FI patent a capacitive humidity detector is described in which the dielectric insulating material is a polymer film whose permittivity is a function of the amount of water absorbed by the polymer film.

The substantial construction of the humidity detector described in said FI patent is a thin plate, onto whose face a structure sensitive to humidity has been processed. A drawback in this prior-art construction is the scattering of the permeability to water of the surface electrode and the resulting scattering of speed of the detector. Further, the size of the construction is quite large, which produces a radiation error especially in radiosonde operation, because the face subjected to solar radiation is considerable and its ventilation is relatively poor. Since, in said prior-art detector, the active face is straight, water tends to remain on this face as drops.

The processes of manufacture of the prior-art impedance detectors and equivalent have been complicated, frequently poorly suitable for automation and poorly suitable for continuous processes of manufacture. The prior-art processes of manufacture of said detectors have been demanding and consisted of a number of steps, in particular in an attempt to obtain a detector as rapid and accurate as possible, which usually requires very small size and precise dimensioning from the constructions and good control of the various parameters in the processes of manufacture.

With respect to the most recent development work carried out by the applicant, related to and closely connected with the present invention, reference is made to the following FI Patents: No. 92,441 (Pat. Appl. No. 921449, filed Apr. 1, 1992), No. 92,440 (Pat. Appl. No. 933701, filed Aug. 23, 1993) and No. 92,439 (Pat. Appl. No. 934268, filed Sep. 29, 1993), and to the FI Patent Application No. 933702 (filed Aug. 23, 1993). The constructions and methods described in said applications can, where applicable, also be used in combination with the present invention.

The process and the detector construction described in the applicant's FI Patent No. 92,441 (Pat. Appl. No. 921449, filed Apr. 1, 1992 became public Oct. 4, 1993) (equivalent to U.S. patent application Ser. No. 08/040,129 and to EP Application 93 850 046.9) are also related to the present invention. In said FI patent, an electrical impedance detector is described, in which the active material between its electrodes is expressly a very thin thread-like glass or glass-ceramic fibre prepared by the glass-drawing technique. Said fibre is a glass-ceramic fibre whose drawing into fibreglass thread has been carried out in glassy form whereas the crystallization into the glass-ceramic form has been carried out in a heat treatment. In the glass-ceramic material the active constituent is crystalline barium-strontium titanate $Ba_xSr_{x-1}TiO_3$ or crystalline lead-strontium titanate $Pb_xSr_{1-x}TiO_3$, wherein x is in the range of 0 ... 1, and which is placed in a glass matrix. The cross-sectional shape of the detector thread is substantially circular, and its diameter is of an order of 25 ... 500 μm.

The construction of the detector described in said FI Patent 92,441 is preferably coaxial, comprising a solid central electrode wire or an equivalent hollow electrode wire and a glass or glass-ceramic layer placed around said electrode, on which layer there is a hermetic glass layer, and on it an electrode layer and/or electrode fibres which have been applied in a separate step. Said detector may be composed of two detector fibre threads, which are joined together by means of a parallel joint, e.g. an adhesive joint, over a certain length. Further, in said FI patent application, a method is described for the manufacture of electrical impedance detectors, which method comprises a combination of the following steps: a continuous detector-fibre thread of substantially circular section is manufactured by means of a glass-drawing technique in itself known out of a molten glass mix which has been alloyed with an additive or with additives that provide(s) the active material of the detector with suitable electrical properties; the detector-fibre thread is crystallized by means of heat treatment into a glass-ceramic form or its material is chosen or otherwise treated so that an active detector material is produced whose capacitance and/or resistance depend on the temperature or, in particular cases, on the amount of water absorbed by the active material; and, for individual detectors, said detector-fibre thread is cut-off into suitable pieces of detector-fibre thread, to which terminals are connected, and/or to whose electrodes, which have been provided at the thread-drawing stage, terminals are coupled or connected, between which terminals the impedance of the detector can be measured.

In the process of said FI Patent 92,441 described above, the drawing of the detector fibre thread is carried out by using a double-crucible process known in itself from the manufacture of optical fibres, in which process, in the inner crucible, molten core glass is used, to which strontium, barium and titanium oxide and/or an equivalent other additive have been added, and in the outer crucible molten glass material is used, such as aluminosilicate glass, from which a tubular hermetic outer layer is obtained onto the detector fibre thread. In the process of said FI patent, into the molten detector fibre, an electrode wire is fed, or the inner electrode is passed into a glass-tube blank, which are then together drawn into a detector fibre thread, or first a hollow detector fibre thread is prepared and its interior is metallized afterwards. In said process, the detector fibre thread is coated with a conductive electrode layer by passing the fibre thread through a crucible with a hole in its bottom and through an oven, said crucible containing conductive paste as the coating paste. Onto the fibre thread, conductor patterns are applied by vapor-deposition or by a photolithographic method. In the process, from the continuous detector fibre thread, pieces of about 1 . . . 5 cm are cut off, which pieces are joined together side by side by means of a longitudinal joint, or detector wires are attached to both sides of a piece of detector fibre thread. In the process of said FI application, the electrode wire does not operate as a carrier or drawing wire in the process of manufacture, said carrier or drawing wire being expressly a fibreglass thread.

The impedance detector and the process of manufacture of same described in the applicant's said FI Patent No. 92,439 are most closely related to the present invention. Said prior-art detector is mainly characterized in that the detector is composed of pieces cut-off out of a continuous detector filament, which detector filament comprises a conductive electrode wire or an assembly of electrode wires, on and/or between which there is an active material whose impedance properties are a function of the physical quantity to be measured.

On the other hand, the process of manufacture described in said FI Patent 92,439 is mainly characterized in that the process comprises a combination of the following steps: detector filament is manufactured as a continuous drawing process by using a conductive electrode wire or an assembly of electrode wires as a carrier wire and as drawing means; in a continuous filament process, said electrode wire or assembly of electrode wires is coated with an active material whose impedance properties are a function of the physical quantity to be measured; and, out of the continuous detector filament prepared in accordance with the steps defined above, pieces of a length suitable for the purpose of use are cut off, the electrode wire or wires being uncovered from one or both ends of said filament pieces so as to form electrical contact points for the impedance detector.

In said FI Patent No. 92,439, primarily a process has been described in which the drawing of the electrode wire takes place from molten glass. In this process, it is a drawback that the drawing cannot be carried out at the room temperature, but the temperature must be higher than 1000° C. Also, the equipment for carrying out the process is quite complicated, and the process is difficult to control. In the process described in said FI Patent 92,439, the detector filaments must be separated from each other, and any extra legs must be removed, which is the most difficult step in the manufacture of detector constructions and which is the step whose automation is most difficult.

The object of the present invention is further development both of the constructions and of the processes of manufacture of the prior-art impedance detectors so as to avoid the drawbacks mentioned above and to achieve the objectives mentioned herein and those that will come out later.

On the other hand, in the present invention, where applicable, advantageous process steps and features of construction and properties involved in the prior art developed by the applicant and described above are also supposed to be utilized so as to achieve the objectives stated in the FI patents mentioned above.

In view of achieving the objectives stated above and those that will come out later, the electrical impedance detector in accordance with the present invention is mainly characterized in that the different electrode wires of the detector filament in the pieces of detector filament have been cut off at different points, compared with one another, so that the impedance to be measured will be formed in the area between said cut-off points of the electrode wires.

On the other hand, a first embodiment of the process of manufacture of a detector in accordance with the invention is mainly characterized in that, as the starting material of the active material layer, a glass paste is used, through which the pair of electrode wires or the equivalent assembly of electrode wires is drawn through the drying oven onto the receiving frame, and that the stage of crystallization of the active material layer takes place in a separate heat-treatment stage which takes place after the winding stage.

On the other hand, a second embodiment of the process of manufacture of a detector in accordance with the invention is mainly characterized in that substantially all, preferably all, steps of treatment and processing applied to the pair of electrode wires coated with the active material layer in the detector filament are carried out when the detector filament is placed on the same flat and plate-shaped frame onto which the detector-filament blank was wound from its coating stage, and that, after the above steps of treatment and processing, the windings of detector filament are cut off from both of their ends placed at the sides of said frame, whereby finished or almost finished pieces of detector filament are formed.

In the detector in accordance with the invention, the electrode wires placed at both ends of the piece of detector filament can be preferably uncovered and connected to the same potential and connector part, in which case the stage of separation of the electrode wires or the removal of extra wires are not needed at all, which steps of work are time-consuming and difficult to make automatic.

When, in the process of the present invention, a glass paste is used as the starting material for the active glass material and when the crystallization of this material is carried out after the stage of winding of the coated filament blank on the same frame on whose support also other steps of treatment and processing of the detector-filament blanks are carried out, a more advantageous process of manufacture is provided, whose advantages will be described in more detail in the following.

In the drawing from molten glass, described in the above FI Patent 92,439, making the filament thinner is limited by the high temperature that is used. At a high temperature, the tensile strength of the filament becomes lower, in which case a very thin filament is no longer strong enough in the drawing process but is broken. Thus, at a lower temperature, it is possible to use a filament that is substantially thinner.

Compared with the process described in said FI patent, the embodiment of the present invention in which glass paste is used has the following advantages:

The drawing can be carried out at the room temperature, whereas, in drawing from molten glass, the temperature must be >1000° C. Then, in the present invention, a thinner filament can be used, whose tensile strength is higher at a low temperature. The result is a detector with a smaller diameter, which detector is preferable expressly in radiosonde applications because of its high speed and lower radiation error.

The equipment is simpler.

The process is easier to control.

Glass paste can be removed (before sintering) from the ends of the detector simply by dissolving.

In a particularly advantageous embodiment of the invention, expressly a plate-shaped and flat frame is used, onto which the detector filament is wound as spiral-shaped after the coating stage, and, when the detector-filament blank is placed on said frame, it is subjected to all the other steps of treatment, such as crystallization of the active material, cutting of the electrode wires, uncovering of the electrode wires, taking place at the ends of the straight draws of the electrode wire between the sides of the frame and preferably taking place by dissolving, and coating of the electrode wires with a layer of protective glass or equivalent, at least in the area of formation of the impedance to be measured. Only after completion of all the above steps are the pieces of electrode wires separated from said frame by cutting off the electrode wires at the sides of the frame at both ends of the wire windings.

In the present invention, as the glass material for the glass paste, preferably aluminoboratic glass is used, whose mode of preparation and whose composition are equal to those described in said FI Patents 92,441 and 92,439.

In this connection, it should be emphasized that, in the coating stage defined above, coating does not necessarily mean that the active material surrounds the electrode wires completely, even if that is preferable.

In the present invention, the electrode wire, preferably a pair of electrode wires or an equivalent assembly of electrode wires, operates in the process of manufacture as a drawing and carrier wire, which receives the tensile strains necessary in the process of manufacture and which electrode wire or assembly or wire gives the finished detector a substantial proportion, preferably the principal proportion, of its mechanical strength. In the process of the present invention, the other layers and parts of the detector are processed and made to adhere expressly into connection with the electrode wire or assembly of wires and not into connection with a fibreglass thread, which is the case, e.g., in the process and detector in accordance with the FI Patent 92,441.

In the following, the invention will be described in detail with reference to some exemplifying embodiments of the invention illustrated in the figures in the accompanying drawing, the invention being by no means strictly confined to the details of said embodiments.

FIG. 5 illustrates a piece of a detector-filament blank, whose electrode wires have been cut in accordance with the invention by means of the device shown in FIG. 4.

FIG. 6 is a central axial sectional view of a finished detector in accordance with the invention taken in the plane C—C shown in FIG. 3B.

In the process and impedance detector in accordance with the present invention, as the active material, a glass ceramic is used, in which the active constituent in the glass matrix is, for example, crystalline barium-strontium titanate $Ba_xSr_{1-x}TiO_3$ or crystalline lead-strontium titanate $Pb_xSr_{1-x}TiO_3$, wherein x is in the range of 0 ... 1. The preparation and the composition of the aluminoborate-based glass used in the detector are preferably similar to those described in the applicant's said FI Patents Nos. 92,441 and 92,439.

Figure 1:
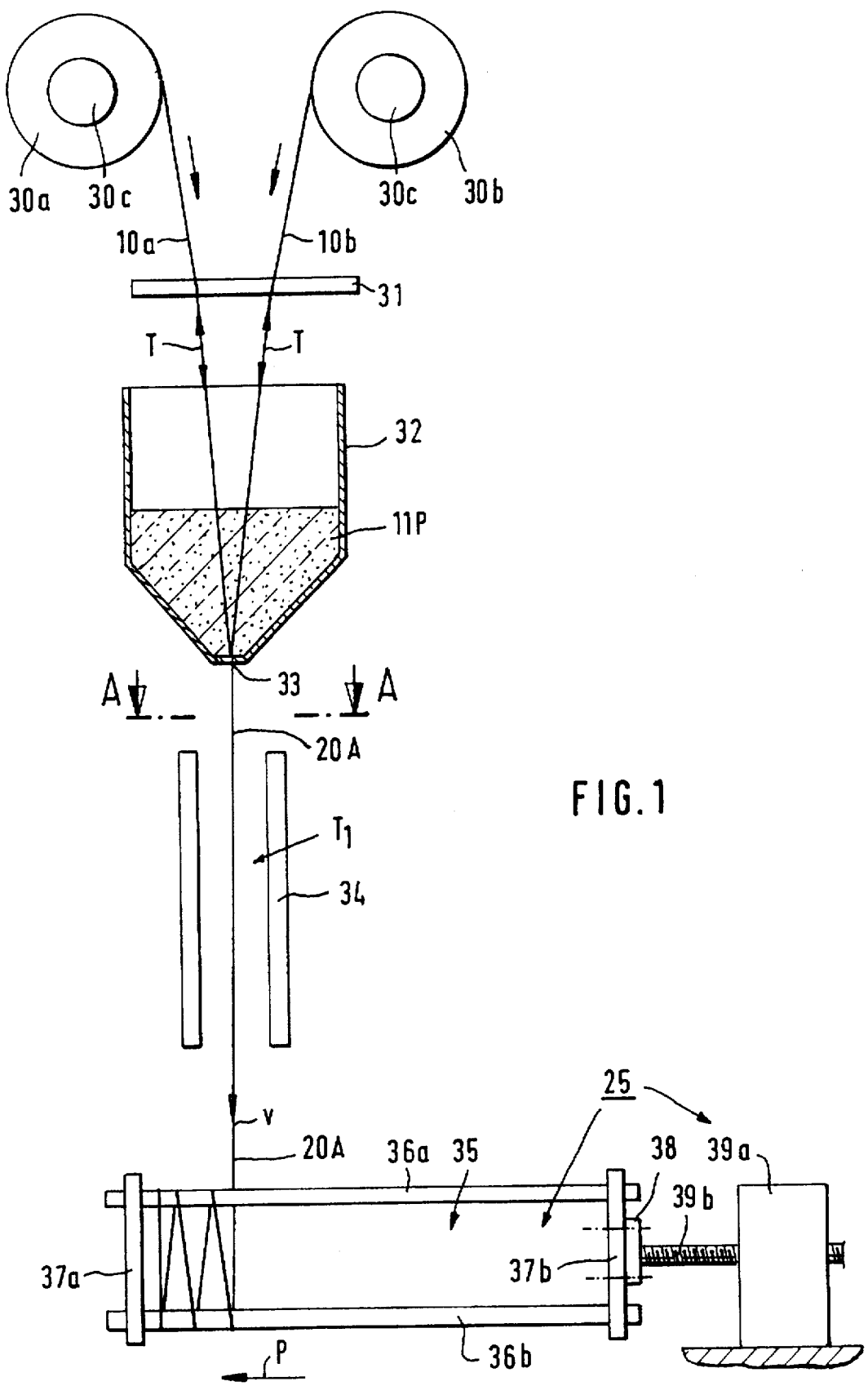
FIG. 1 is a schematic illustration of the process step in accordance with the invention in which the pair of electrode wires is drawn from a pair of starting reels onto the arrival frame through a wire guide and through a crucible that contains glass paste.

According to FIG. 1, the manufacture of the detector filament takes place by using the pair of electrode wires 10a and 10b as the carrying wire and drawing means in the continuous filament process, which wires are drawn from starting reels 30a and 30b, which are provided with friction brakes 30c, through a quartz crucible 32. The, for example, aluminoborate-based glass material 11P present in the quartz crucible 32 is prepared by means of methods known from thick-film technology, for example, as follows:

the glass is ground in a ball mill, and it is mixed with an organic constituent, whose composition is, for example, ethyl cellulose (4%-wt.), Antharox (1.3%-wt.), and terpineol (94.7%-wt.). With the above composition, a suitable viscosity is obtained when the proportion of glass powder is ~80%-wt. and that of the organic constituent ~20%-wt.

The drawing crucible 32 is manufactured, for example, out of a quartz tube, whose end is drawn into a sharp-tipped cone. The end of the cone is cut off so that a bottom hole 33 of the crucible 32 is formed, whose diameter is about 0.3 mm. The electrode wires 10a,10b, for example platinum wires of a diameter of 25 µm, are wound onto feed reels 30a,30b provided with friction brakes 30c, which reels are placed in the drawing device. The ends of the wires 10a,10b are threaded through the wire guide 31, the bottom hole 33 of the quartz crucible 32, and through the drying oven 34 and are fixed to the frame 35 placed in the winding device 25.

Onto the bottom of the crucible 32, glass paste 11P is poured. The winding device 25 is started, whereby its motor 39a starts rotating the frame 35 and, at the same time, pulls the electrode wires 10a,10b through the crucible 32 at a uniform speed v. When passing through the crucible 32, the electrode wires 10a,10b are coated fully with the glass paste 11' (FIG. 3A), which is dried as the filament 20A passes through the tubular oven 34, in which the temperature is $T_1 \approx 100°$ ... 150° C. During the winding, at the same time, the winding device 25 shifts the frame 35 slowly in the transverse direction (arrow P) so that the filament 20A is wound as screw-shaped over the entire length of the frame 35 in the way shown in FIG. 2.

The winding device 25 is accomplished, for example, in the way shown in FIG. 1, so that the winding device 25 includes a screw motor 39a, which rotates a screw 39b, which is provided with a threading and to which the frame 35 is attached by means of a fastening part 38, for example a suitable snap joint. The speed of rotation of the plane and flat frame 35 can be arranged in such a way cyclically varying, for example as sine-formed, that the drawing speed v of the filament 20A remains invariable. The motor 39a shifts the screw 39b in the direction of the arrow P as the winding of the filament 20A makes progress. Many other embodiments of the winding device 25, which may differ from that shown in FIG. 1 to a substantial extent, are also possible and included in the scope of the invention.

A system that keeps the drawing speed invariable is, however, not necessarily needed in the winding device. The winding device may revolve at an invariable speed, in which case the drawing speed varies as sine-formed. Correspondingly, the coating thickness varies to some extent periodically. The distance of the frame 35 from the crucible 32 is dimensioned so that the portions of the filament that are drawn more slowly and that, consequently, have a thicker coating are placed at the edges of the frame 35. In the middle of the frame 35, in the active part of the detector, the coating thickness shows little variation. Said variation is not detrimental in the manufacture of the detector, nor does it deteriorate the reproducibility of the manufacturing process, because it is repeated equally in the case of each detector.

Figure 3A:
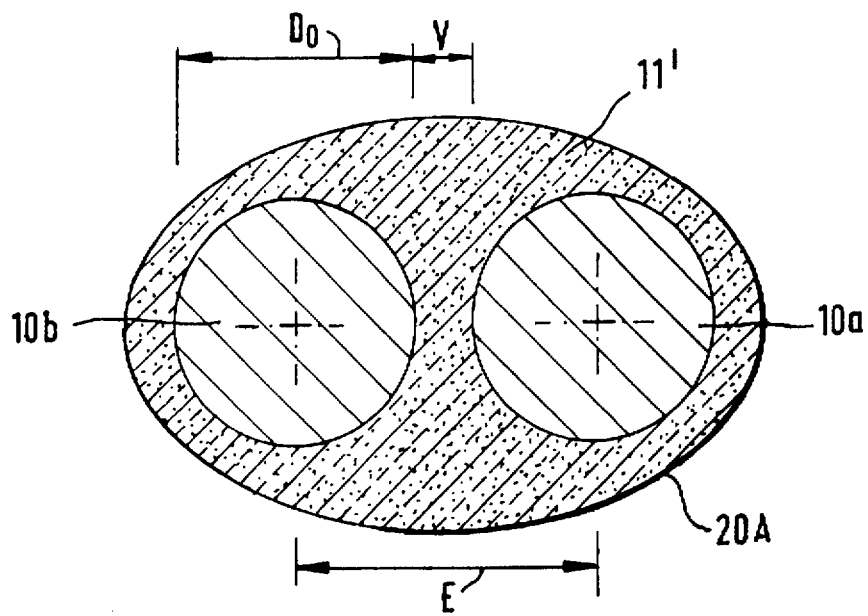
FIG. 3A is a sectional view of the detector-filament blank taken along the lines A—A in FIGS. 1 and 2.

FIG. 3A is a sectional view of a coated filament 20A after drawing. By regulating the friction brakes 30c in the reels 30a,30b (draw tension T), the location of the wire guide 31, the drawing speed v, and/or the temperature $T_1$, it is possible to affect the distance V between the electrode wires 10a,10b. A suitable distance V, when electrode wires 10a,10b of a diameter of $D_0 \approx 25$ μm are used, is $V \approx 5 \ldots 10$ μm. The distance E between the centres of the electrode wires is $E = D_0 + V$, i.e., with the dimensions given above, $E \approx 30 \ldots 35$ μm. By means of suitable choices of the above parameters $T_1, v, D_0$, an optimal twin-wire filament 20A is obtained so that the diameter of the detector and, at the same time, its radiation error and response time can be made as little as possible.

Figure 2:
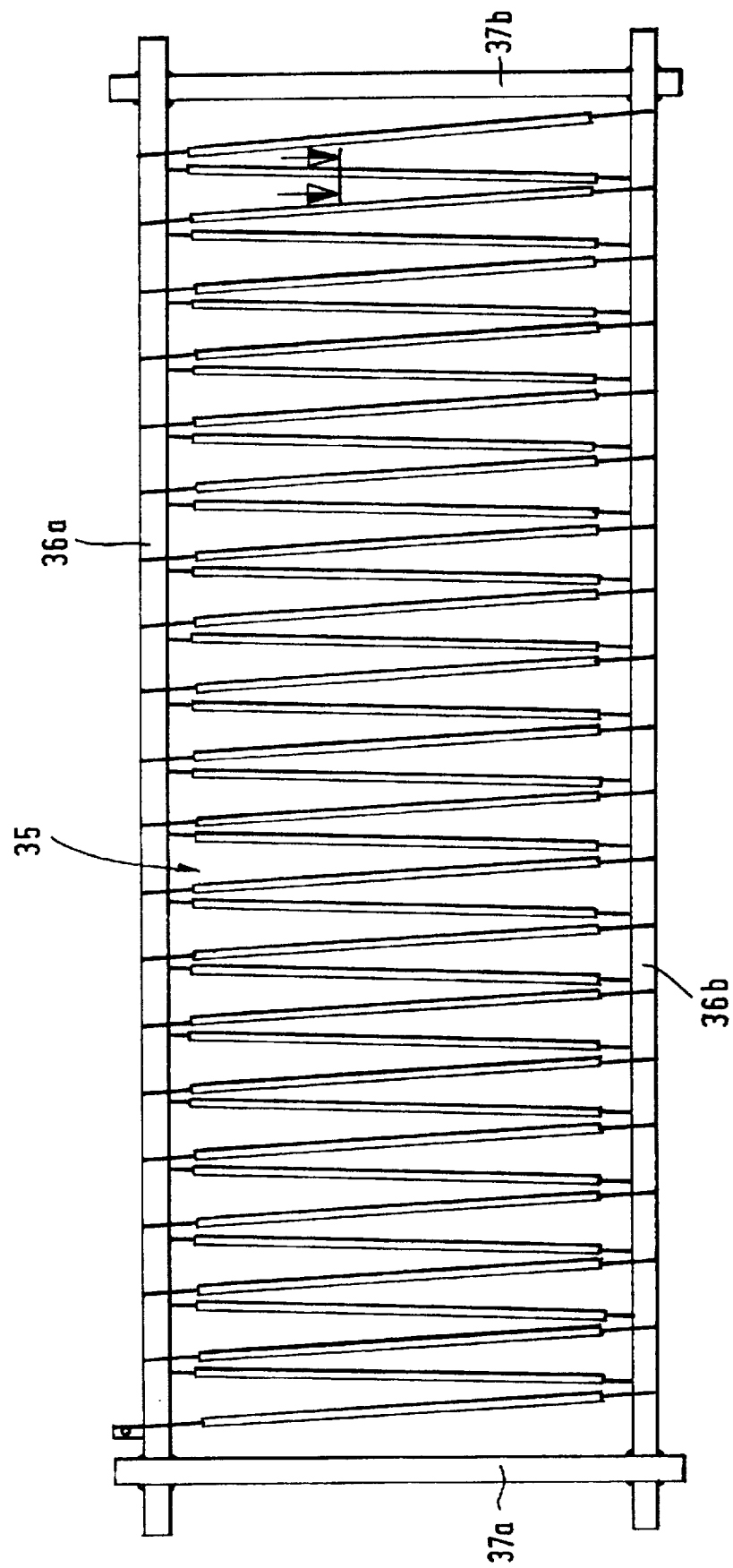
FIG. 2 shows a fully wound detector-filament frame, which frame for detector filament is also seen in FIG. 1.

The winding frame 35 shown in FIGS. 1 and 2 has been manufactured by welding out of four thin, e.g., 2 mm metal rods 36a,36b and 37a,37b. A suitable material for the longer sides 36a and 36b of the frame is such a metal, for example nickel, on whose face an oxide layer is formed during heat treatment. The oxide binds the filament 20A to the frame so that, in the later stage of separation of the detector blanks, they can be separated one by one without discharge of the entire filament 20A off the frame 35. For the shorter sides 37a and 37b of the frame 35, a metal is suitable best whose thermal expansion coefficient is substantially the same as that of the electrode wires 10a,10b, and, when platinum wires 10a,10b are used, a suitable material is, for example, titanium. The frame 35 is disposable.

After the filament has been wound onto the frame 35, paste is removed from the ends 42a,42b of the detector blanks (FIG. 6) over a distance of, for example, about 1 mm by sinking the frame 35, with the long sides 36a and 36b ahead, into an ultrasound washer (not shown) filled with a suitable solvent (e.g. xylene). The purpose is to uncover the ends 42a,42b of the electrode wires 10a,10b so that the contacts at the stage of connecting of the detector 40 are made reliably.

The crystallization of the glass-ceramic material 11' on the detectors 40 also takes place on support of the same frame 35 by means of a heat treatment similar to that described in the FI Patent 92,439. In the method in which a glass paste 11P is applied, in the first stage of the heat treatment (lower temperature, for example 1 h at 500° C.) sintering of the glass paste takes place. In the second stage (higher temperature, for example 1 h at 950° C.) the glass is crystallized into a glass-ceramic which has dielectric properties suitable for the impedance detector.

After the stage of crystallization of the glass-ceramic material 11', in the cutting stage, which is still carried out on the frame 35, each electrode wire 10a and 10b in the two-wire filament 20B is cut off at one point 41a and 41b so that four parts D, E, F and G are formed (FIG. 5), which are bound together by the glass-ceramic 11 placed in between in the way shown in FIG. 5. The active part of the detector 40, i.e. the capacitor to be measured, is formed in the area CV between the cutting-off points 41a and 41b, in which area the electrode wires 10a and 10b are placed overlapping each other. The detector 40 will be connected to its place of operation from its ends so that both wires 10a,10b are contacted with the same electrode (FIG. 6) at each end of the detector. Then the pieces D and E and the pieces F and G, respectively, will be at the same potential during the measurement.

Figure 4:
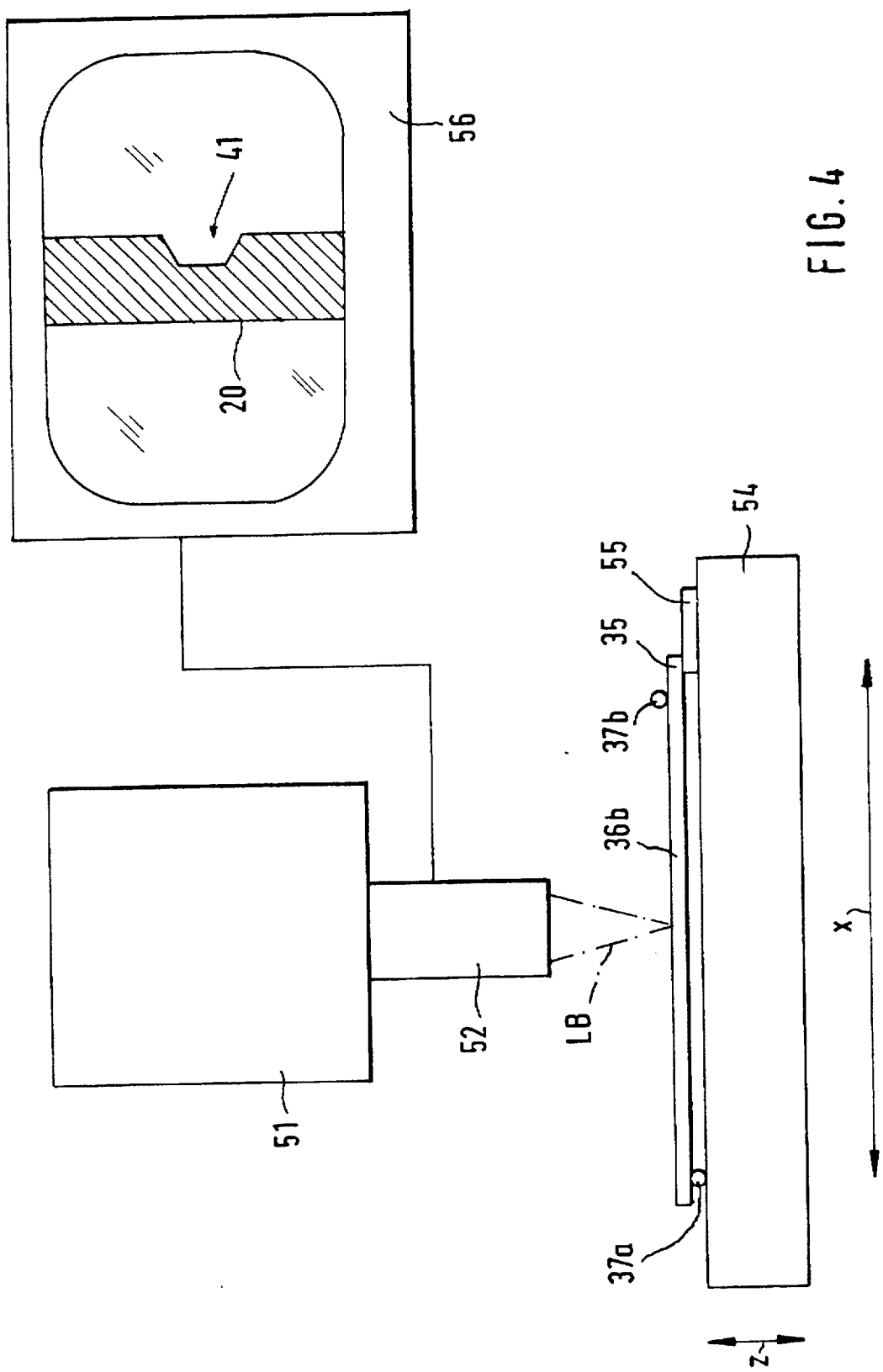
FIG. 4 is a schematic side view of a laser device used for cutting the metallic electrode wires.

Said cutting-off stage is carried out, for example, in accordance with FIG. 4 by placing the detector frame 35 on the XYZ-table 54 and by directing the laser 51 beam LB at the cutting point onto one of the electrode wires 10a,10b either manually by means of the monitor 56 or by using a machine-sight system. For the cutting, a laser is used, e.g. a pulsated Nd/YAG-laser designed for machining use. This laser includes a cutting head, which includes collimation of the laser beam and the optics necessary for the alignment. The electrode wire 10a,10b is cut off by shooting one pulse by means of the laser 51. After this the beam LB of the laser 51 is aimed again at the other cut-off point 41a/41b, and a second cutting-off is performed. In this way, all the electrode wires 10a,10b of the detector blanks placed at the top side of the frame 35 are cut off, after which the frame 35 is turned over, and the same procedure is applied to the detector blanks at the opposite side of the frame.

Figure 3B:
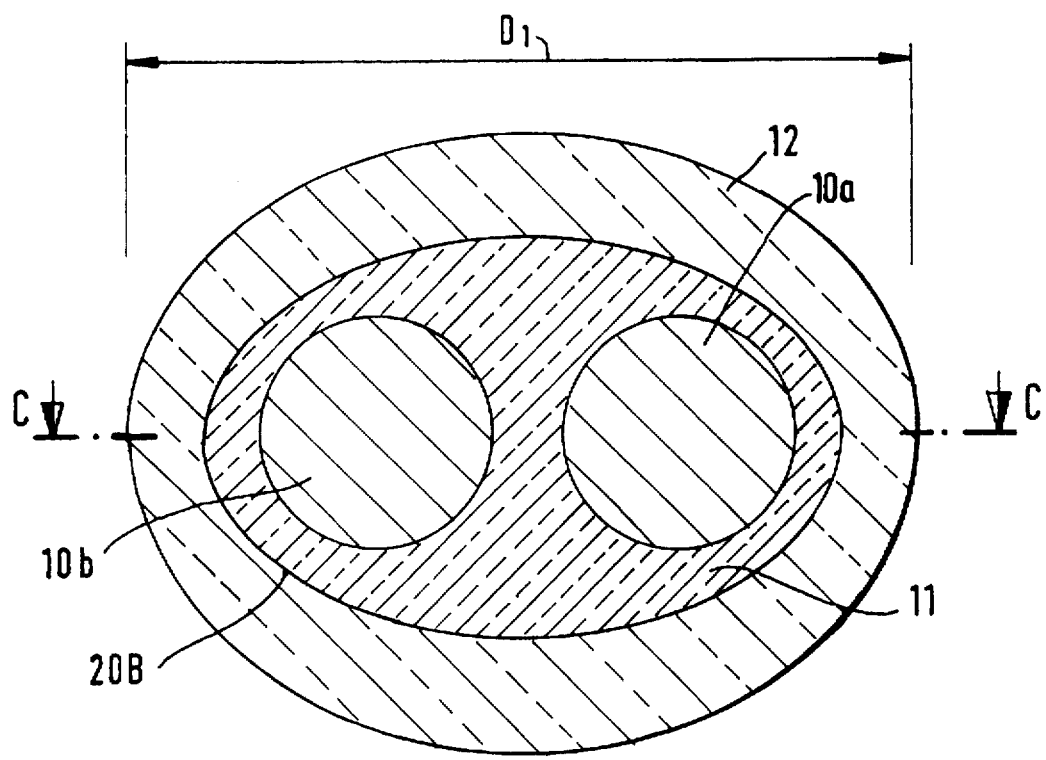
FIG. 3B is a sectional view of a finished impedance detector as shown in FIG. 6, taken along the line B—B in FIG. 6.

The active part of the detector 40 must be protected hermetically from moisture. This is carried out by coating the middle part of the detector 40 with a layer of glass 12 (FIGS. 3B and 6). For the glass layer, a glass paste is used, in which the glass component is some glass whose thermal expansion coefficient is close to that of platinum, such as lead glasses intended for platinum/glass joints, which are available from a number of manufacturers. The organic component in the paste can be the same as in the glass-ceramic paste mentioned above. It is also possible to use ready thick-film pastes intended for hermetic encapsulation. The protective glass paste is spread onto the middle portion of the detector by spraying. As a rule, several, for example four, times of spraying are required from different directions around the filament 20B. The paste is dried and sintered by using a temperature profile suitable for the paste concerned. The thickness of the protective glass layer 12 is $10 \ldots 50$ μm when Pt wires 10a,10b of $D_0 \approx 25$ μm are used, depending on the paste that is used. Then, the overall thickness of the detector 40 becomes $D_1 \approx 100 \ldots 150$ μm. In FIG. 6, axial lengths $L_1$, $L_2$ and $L_3$ of the detector and of its different parts are indicated. These lengths are chosen, while using the other dimensions given above, e.g., as follows: $L_1 \approx 20$ mm, $L_2 \approx 6$ mm, and $L_3 \approx 2$ mm.

According to FIG. 3B, the cross-sectional shape of the detector filament 20B and of the finished detector 40 is elliptical at the protective layer 12 so that the larger diameter $D_1$ is placed at the centres of the electrode wires 10a,10b. Other cross-sectional shapes of the detector filament 20B, besides those shown in the figure, are also possible.

In stead of a pair of electrode wires 10a,10b, it is also possible to use a different assembly of electrode wires, which can also be cut off in a way different from that shown in FIGS. 5 and 6. Then, the capacitance to be measured can be formed in different ways from connections in series and/or in parallel of component impedances fitted over the length of the detector filament 20.

It is only after all of the steps described above that the detector blanks are separated from the frame 35 by cutting the detector filaments 20 one at a time from both ends near the frame 35 at points from which the glass layer 11 had been dissolved. In this way, short contact points 42a,42b of uncovered electrode wire 10a,10b remain at the ends of the detectors 40, from which wires the detector can be fixed easily to its place of operation by soldering or by means of a conductive adhesive.

The advantage of the detector construction described above in comparison to the constructions described in the FI Patent 92,439 is therein that the electrode wires need not be separated from one another and that extra legs need not be removed. This stage is most difficult and the stage most difficult to automatize in the manufacture of the detector constructions described in said patent. The novel construction also makes the detector substantially easier to manufacture in this respect.

The invention is by no means strictly confined to the process steps described above or to their relative sequence, nor to the details of the detector-filament blank 20B or of the finished detectors. For example, the relative sequence of the process steps may vary to some extent, and the details of the detector may also vary, for example, so that more than two electrode wires are used, even if such variations are, as a rule, not advantageous. However, according to the present-day estimation, the preferred embodiment is obtained when one pair of electrode wires 10a,10b is used, which wires are cut off in the way coming out from FIGS. 5 and 6.

In the following, the patent claims will be given, and the various details of the invention may show variation within the scope of the inventive idea defined in said claims and differ from what has been stated above by way of example only.

We claim:

1. A process for manufacture of electrical impedance detectors (40) intended for measurement of a predetermined physical quantity, in which process a detector filament (20) is manufactured as a continuous drawing process by using an electrically conductive pair of electrode wires (10a, 10b) as a carrier wire and as a drawing means; and coating said pair of electrode wires (10a, 10b) with an active material (11') whose impedance properties are a function of the physical quantity to be measured, and, out of the detector filament (20) obtained in the steps defined above, cutting through electrode wires to form filament pieces of a length suitable for the purpose of use, and uncovering the electrode wires (10a,10b) from both ends of said filament pieces so as to form electrical contact points (42a,42b) for the detector (40), characterized by the steps of:

drawing the pair of electrode wires (10a,10b) through a paste (11P) comprising a starting material of the active material layer (11') and then through a drying oven (34) to produce a filament (20) with a coating of the starting material; and then winding the filament (20) onto a receiving frame (35);

processing the active material layer in a separate heat-treatment step that takes place after the winding step; and forming at least one detector from the filament (20) by cutting through the electrode wires (10a,10b) at different points (41a,41b) compared to one another, so that the impedance (CM) to be measured is formed between the cutting locations.

2. The process as in claim 1, wherein:
the step of drawing comprises drawing the pair of electrode wires through a glass paste, and
the step of processing comprises crystallizing the glass paste in a separate heat-treatment step after the step of winding the filament wire onto the receiving frame.

3. A process as claimed in claim 2, characterized in that said step of crystallization of the glass paste is carried out on a flat and plate-like frame (35) comprising the receiving frame onto which the filament (20) was wound.

4. A process as claimed in claim 2, characterized in that the crystallization of the active material takes place in two different heat-treatment stages, of which, in the first step, at a relatively lower temperature, the glass paste is sintered, and in the second stage, which takes place at a relatively higher temperature, the glass material is crystallized into a glass-ceramic material, which has dielectric properties suitable for the impedance detector.

5. A process as claimed in claim 2, characterized in that the cutting step mentioned above is carried out, on a flat and plate-like frame comprising the receiving frame onto which the filament (20) was wound after its coating step.

6. A process as claimed in claim 1, characterized in that the electrode wires (10a, 10b) in the pieces of detector filament (20) are cut off at different points (41a, 41b), compared with one another, so that the impedance (CM) to be measured is formed between the cut-off points (41a, 41b).

7. A process as claimed in claim 1, characterized in that, after said winding step, paste is removed from the ends of successive straight portions of the detector filament (20) over a short portion by sinking said frame (35), with its long side (36a, 36b) ahead, into a solvent operative to form uncovered connecting points of the electrode wires (10a, 10b) at both ends of the pieces of detector filament (20).

8. A process as claimed in claim 7, characterized in that said step of removing paste is carried out in an ultrasound washer.

9. A process as claimed in claim 1, characterized in that said step of cutting through the electrode wires is carried out by means of a laser beam (LB) while the electrode wire is fixed on said frame (35), so that all the electrode wires (10a, 10b) in the filament blanks (20) placed at the top side of the frame are cut through after which the frame (35) is turned over, and the same steps of cutting are applied to the electrode wires (10a, 10b) at the opposite side of the frame.

10. A process as claimed in claim 1, characterized in that an active part of the detector is protected hermetically from moisture by applying onto said part a protective glass layer (12), by applying protective glass paste onto a middle portion of the detector by spraying and by thereupon drying and sintering the protective glass paste.

11. A process as claimed in claim 1, characterized in that the step of cutting the detector filament (20) into separate pieces of detector filament is carried out when the detector filament (20) is placed as wound on said same frame (35).

12. A process as claimed in claim 1, characterized in that, as said frame (35), a rectangular frame is used which is composed of thin metal wires, the filament (20) being wound as spiral-shaped around long sides (36a, 36b) of said frame while said frame (35) is rotated around a central axis parallel to its long sides and while the frame is, at the same time, displaced (p) in the direction of said axis.

13. A process for manufacture of electrical impedance detectors (40), said detector (40) being intended for measurement of a predetermined physical quantity, in which process a detector filament (20) is manufactured as a continuous drawing process by using an electrically conductive pair of electrode wires (10a,10b) as a carrier wire and as a drawing means; and coating said pair of electrode wires (10a,10b) with an active material (11') whose impedance properties are a function of the physical quantity to be measured, and, out of the detector filament (20) obtained in the steps defined above, cutting off pieces of a length suitable for the purpose of use, the electrode wires (10a,10b) being uncovered from both ends of said filament pieces so as to form electrical contact points (42a,42b) for the detector (40), characterized in that:

the detector filament is wound on a flat frame (35), steps of treatment and processing applied to the pair of electrode wires (10a,10b) coated with the active material layer (11') in the detector filament (20) are carried out while the detector filament is in place on the frame (35) onto which the detector filament (20) is wound from the step of coating, and that;

after the steps of treatment and processing, the windings of the electrode wires (10a,10b) comprising the detector filament are cut off from both ends located at sides (36a,36b) of said frame, whereby substantially finished detectors (40) are formed.

14. A process for manufacturing an electrical impedance detector for measuring either temperature or humidity, comprising the steps of:

forming a continuous detector filament (20) by coating a pair of electrically conductive electrode wires (10a, 10b) with an active material (11) whose impedance properties are a function either of temperature or humidity, so that the active material is on and between the electrode wires; and then separating from the continuous filament at least one detector having opposite ends by cutting the pair of electrode wires (10a,10b) at different points (41a,41b) compared with one another, between the opposite ends, so that the impedance to be measured is formed in an area (CV) between the cutting locations of the electrode wires.

* * * * *